United States Patent [19]

Felton et al.

[11] 4,179,518
[45] Dec. 18, 1979

[54] SYNERGISTIC PESTICIDAL COMPOSITION

[75] Inventors: John C. Felton, Sittingbourne; John S. Badmin, Isle of Sheppey; Roland S. Twydell, Rodmersham, all of England

[73] Assignee: Shell Oil Company, Houston, Tex.

[21] Appl. No.: 873,309

[22] Filed: Jan. 30, 1978

Related U.S. Application Data

[63] Continuation-in-part of Ser. No. 820,269, Jul. 29, 1977, abandoned.

[51] Int. Cl.² .............................................. A01N 9/02
[52] U.S. Cl. ................................... 424/300; 424/304; 424/327; 424/298

[58] Field of Search .................... 424/300, 304, 327

[56] References Cited

U.S. PATENT DOCUMENTS 3,835,176 9/1974 Matsuo et al. ....................... 424/304
3,996,244 12/1976 Fujimoto et al. ................... 424/285

Primary Examiner—V. D. Turner

[57] ABSTRACT

A pesticidal composition comprising
(a) S-methyl N-(methylcarbamoyloxy)thioacetamidate and
(b) at least one pesticidally active α-cyanobenzyl phenylacetate.

2 Claims, No Drawings

SYNERGISTIC PESTICIDAL COMPOSITION

CROSS-REFERENCE TO RELATED APPLICATIONS

This application is a continuation-in-part of U.S. Ser. No. 820,269, filed July 29, 1977, now abandoned.

BACKGROUND OF THE INVENTION

1. Field of the Invention

This invention relates to a pesticidal composition comprising S-methyl N-(methylcarbamoyloxy)thioacetamidate and certain α-cyanobenzyl phenylacetates.

2. Description of the Prior Art

Certain cyclopropane carboxylic acid derivatives are a useful class of pesticides called "pyrethroids" which have been of considerable interest because of their quick knockdown activity, low persistence as toxic residues and their low mammalian toxicity. Certain derivatives of phenylacetic acids have also been found to have properties of the pyrethroid type. Unfortunately, while such compounds are desirable pesticides, they tend to be difficult or expensive to manufacture due to their relatively complex chemical structures.

U.S. Pat. No. 3,835,176 discloses insecticidal compositions containing certain carbamates with certain α-cyanobenzyl cyclopropane-carboxylate.

Applicants have found that combinations of certain α-cyanobenzyl phenylacetate pyrethroids with S-methyl N-(methylcarbamoyloxy)thioacetamidate as hereinafter described possess synergistic activity with respect to acarid pests, that is to say the activity of the combination of the two pesticides produces a more-than-additive pesticidal effect.

SUMMARY OF THE INVENTION

The present invention provides a pesticidal composition comprising
(a) S-methyl N-(methylcarbamoyloxy)thioacetamidate (hereinafter referred to as "methomyl") and
(b) at least one pesticidally active α-cyanobenzyl pyrethroid insecticide having the following formula I

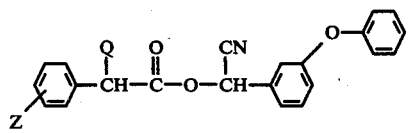

wherein Z represents a halogen atom having an atomic number of from 9 to 35, inclusive, preferably a chlorine atom, or an alkoxy group of 1 to 4 carbon atoms, e.g., methoxy, Q represents an alkyl group of 1 to 6 carbon atoms, especially a branched chain group, such as an isopropyl group.

It should be noted that optical isomers of the compounds according to formula I are within the scope of the present invention as well as racemates and mixtures of isomers of one or more of the pesticidally active compounds according to formula I. The various isomers of the compounds according to formula I may have different insecticidal toxicities and/or knockdown potency. Thus, one may prefer to resolve mixtures of isomers to recover a more pesticidally active isomer or racemic mixture or to prepare the more active forms directly for use in the compositions of the invention.

A preferred phenylacetate of (b) for use in the pesticidal composition according to the invention is α-cyano-3-phenoxybenzyl α-isopropyl-p-chlorophenylacetate designated Compound X in the Examples.

The mixture of methomyl and the phenylacetate insecticide not only produces a pesticide having a markedly wider spectrum of activity but also produces a surprising synergistic effect especially with respect to acarids, e.g., glasshouse red spider mite, *Tetranychus urticae*.

The weight ratio of the phenylacetate insecticide (b) to methomyl (a) may be in the range of about 5:1 to 1:50, preferably in the range of about 1:1 to 5:1.

The pesticidal composition according to the invention may also employ a carrier, a surface-active agent or both a carrier and a surface-active agent to facilitate application of the composition to the pest or its habitat at the desired dosage rates.

The term "carrier" as used herein means a solid or fluid material, which may be inorganic or organic and of synthetic or natural origin.

Typical solid carriers include natural and synthetic clays and silicates, for example natural silicas, such as diatomaceous earths and aluminum silicates, for example, kaolinites, montmorillonites, and micas. Typical fluid carriers are ketones, for example, methylcyclohexanone, aromatic hydrocarbons, for example, methylnaphthalenes, petroleum fractions, such as, for example, petroleum xylenes and light mineral oils, and chlorinated hydrocarbons, for example carbon tetrachloride. Mixtures of liquids are often suitable.

One or more surface-active agents and/or stickers can be included in the formulation. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol, condensates of these with ethylene oxide and/or propylene oxide; condensation products of fatty alcohols or alkyl phenols, for example p-octylphenol or p-octyl-cresol, with ethylene oxide and/or propylene oxide; sulphates or sulphonates of these condensation products, alkali or alkaline earth metal salts, preferably sodium salts, or sulphuric or sulphonic acid esters containing at least 10 carbon atoms in the molecule, for example, sodium lauryl sulphate, sodium secondary alkyl sulphates, sodium salts, of sulphonated castor oil, and sodium alkylaryl sulphonates, such as sodium dodecylbenzene sulphonate; and polymers of ethylene oxide and copolymers of ethylene oxide and propylene oxide.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The invention also includes a method of combating pests which comprises applying or administering to the pest or its habitat a pestically-effective amount of the composition according to the invention.

The invention is further illustrated by the following Examples in which the joint action of two pesticides was analyzed according to the method of Yun-Pei Sun and E. R. Johnson, Journal of Economic Entomology, 1960, Volume 53, No. 5, pages 887–892.

Thus, the joint action of two pesticides were analyzed by determining the actual toxicity indices of the components and of mixtures of the compounds by reference to dosage-mortality curves. The theoretical toxicity of the mixture is equal to the sum of toxicity indices calculated from the percentage of each component multiplied by its respective toxicity index. Therefore, the joint toxicity of co-toxicity coefficient of a mixture $$= \frac{\text{Actual toxicity index of a mixture}}{\text{Theoretical toxicity index of a mixture}} \times 100$$

A coefficient of a mixture near 100 indicates probability of similar action by the two pesticides; independent action usually should give a coefficient less than 100, while a coefficient significantly above 100 strongly indicates synergism.

The compound tested in the Examples is shown below:

COMPOUND X

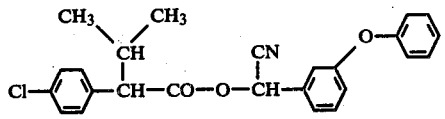

EXAMPLE

Activity of Phenylacetate/methomyl Mixture Against *Tetranychus urticae* (glasshouse red spider mite)

The acaricidal activity of Compound X and its mixture with methomyl was assessed by the following method.

The compounds and mixtures were formulated as solutions or suspensions in water containing 20% by weight of acetone and 0.05% by weight of Triton X-100 as wetting agent. The formulation contained 0.4% by weight of the compound or mixture to be tested and were diluted to produce formulations containing various concentrations. Leaf discs cut from french bean plants were sprayed with the formulations and left for ½–1 hour drying period. Each leaf disc was then innoculated with 10 red spider mites and mortality counts made 24 hours after innoculation. From these results the $LD_{50}$'s (the lethal dose in micrograms of active material to kill 50% of the mite population) could be calculated.

The toxicity indices of the compounds and the mixtures were calculated using the following formula $$\text{Toxicity Index} = \frac{LD_{50} \text{ of standard insecticide parathion}}{LD_{50} \text{ of compound or mixture}}$$

The coefficient of cotoxicities were then calculated according to the method described above. The results are shown in the following table.

| ACTIVITY AGAINST THE GLASSHOUSE RED SPIDER MITE (*TERTRANYCHUS URTICAE*) | | | | |
|---|---|---|---|---|
| | $LD_{50}$ Replicates | | Coefficient of Cotoxicity Replicates | |
| Treatment | 1 | 2 | 1 | 2 |
| Methomyl | 0.033 | 0.039 | — | — |
| Compound X | 0.25 | 0.17 | — | — |
| Methomyl + Compound X (1:4 ratio) | 0.068 | 0.066 | 159 | 154 |

We claim:
1. A composition for combating acarid pests comprising
   (a) S-methyl N-(methylcarbamoyloxy) thioacetamidate and
   (b) an acaricidically active α-cyano-3-phenoxybenzyl α-isopropyl-4-chlorophenylacetate on a ratio of (a) to (b) of from about 1 to 1 to about 1 to 5.
2. A method for combating acarid pests which comprises applying to the pests or to a locus an acaricidally effective amount of a composition according to claim 1.

* * * * *

UNITED STATES PATENT AND TRADEMARK OFFICE
CERTIFICATE OF CORRECTION

PATENT NO. : 4,179,518
DATED      : December 18, 1979
INVENTOR(S) : JOHN C. FELTON, JOHN S. BADMIN and ROLAND S. TWYDELL It is certified that error appears in the above-identified patent and that said Letters Patent are hereby corrected as shown below:

In the left hand column, title page, between items "[63]" and "[51]", insert

-- [30]   Foreign Application Priority Data

February 9, 1977  United Kingdom.....5335/77 --

*Signed and Sealed this*

*Eighteenth* Day of *August 1981*

[SEAL]

Attest:

GERALD J. MOSSINGHOFF

Attesting Officer    Commissioner of Patents and Trademarks